United States Patent
Murata et al.

[11] Patent Number: 5,859,276
[45] Date of Patent: Jan. 12, 1999

[54] ORGANOTRANSITION METAL COMPOUNDS

[75] Inventors: Kunihiko Murata; Junichi Hori; Masahiro Yoshida, all of Saitama-ken, Japan

[73] Assignee: Kanto Kagaku Kabushiki Kaisha, Tokyo, Japan

[21] Appl. No.: 935,422

[22] Filed: Sep. 23, 1997

[30] Foreign Application Priority Data

Oct. 4, 1996 [JP] Japan .................................. 8-281643

[51] Int. Cl.$^6$ .................. C07F 17/00; C07F 7/00
[52] U.S. Cl. .................. 556/11; 556/12; 556/20; 556/26; 556/51; 556/53; 526/160; 526/943; 502/103; 502/117
[58] Field of Search .................. 556/20, 26, 51, 556/53, 11, 12; 526/160, 943; 502/103, 117

[56] References Cited

U.S. PATENT DOCUMENTS

| | | | |
|---|---|---|---|
| 5,103,030 | 4/1992 | Rohrmann et al. | 556/12 |
| 5,391,790 | 2/1995 | Rohrmann et al. | 556/28 |
| 5,495,035 | 2/1996 | Jordan et al. | 556/1 |
| 5,597,935 | 1/1997 | Jordan et al. | 556/11 |
| 5,616,747 | 4/1997 | Rohrmann et al. | 556/11 |

FOREIGN PATENT DOCUMENTS

| | | |
|---|---|---|
| 42-22691 | 11/1967 | Japan . |
| 1-97490 | 1/1989 | Japan . |
| 6-122692 | 6/1994 | Japan . |
| WO 95/32979 | 12/1995 | WIPO . |

OTHER PUBLICATIONS

Johnson et al., Organometallics, vol. 13, pp. 2907–2909, 1994.

*Primary Examiner*—Porfirio Nazario-Gonzalez
*Attorney, Agent, or Firm*—Darby & Darby

[57] ABSTRACT

New metallocene compounds (II) and their synthetic intermediates (I) used for olefin polymerization catalysts represented by the general formulas (I) and (II)

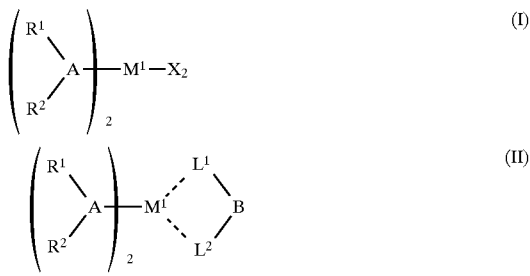

(wherein X can be identical or different and is each independently of one another a halogen atom, $M^1$ is a group IV transition metal atom, A is a nitrogen or phosphorus atoms, $R^1$ is an aryl group, $R^2$ is a saturated hydrocarbon group having 1–10 carbon atoms, whereby each of $R^2$ can bind one another to constitute a ring containing A and $M^1$, $L^1$ and $L^2$ can be each other identical or different and are a substituted cyclopentadienyl, indenyl, substituted indenyl or substituted fluorenyl groups, B is a hydrocarbon having 1–20 carbon atoms, silylene having 1–20 carbon atoms, oligosilylene or germylene groups, binding to $L^1$ and $L^2$, and $M^1$ can be also coordinated with an ether or an amine at any coordination number.).

8 Claims, No Drawings

ORGANOTRANSITION METAL COMPOUNDS

BACKGROUND OF THE INVENTION

The invention relates to new metallocene compounds having the racemic structure, which are useful as olefin polymerization catalyst, and their synthetic intermediates.

Metallocene compounds, in which a cyclopentadienyl, indenyl or fluorenyl groups, or derivatives thereof are made ligands, are useful as polymerization catalysts for olefins such as ethylene, propylene or the like under the coexistence of a cocatalyst, for example, aluminoxane. For the preparation for a stereoregular polyolefin have been examined metallocene compounds having various kinds of stereostructures. For a syndiotactic polyolefin preparation is effective a metallocene compound having the Cs symmetry (*J. Am. Chem. Soc.*, 110, 6255 (1988), whereas it is reported that for an isotactic polyolefin preparation is effective a metallocene compound having the racemic structure (*Angew. Chem. Int. Ed. Engl.*, 24, 507 (1985); *J. Am. Chem. Soc.*, 109, 6544 (1987); *Chem. Rev.*, 92, 965 (1992); *Organometallics*, 13, 954 (1994); *Organometallics*, 13, 964 (1994)).

Conventionally, the synthesis of a metallocene compound having a racemic structure has been carried out by reacting the dianion produced by the deprotonation of the ligand and metal tetrachloride or its tetrahydrofuran adduct (Scheme 1).

Scheme 1

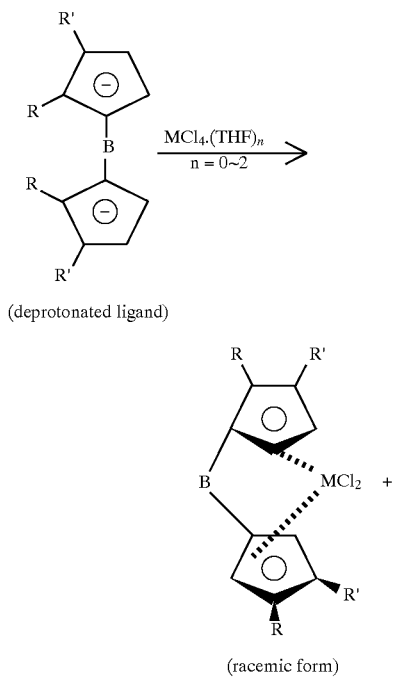

(racemic form)

-continued
Scheme 1

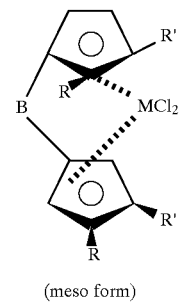

(meso form)

However, since this method gives tarry substances as byproducts, the procedure to separate the aimed metallocene compound having the racemic structure is very tedious (*Angew. Chem. Int. Ed. Engl.*, 24, 507 (1985); *J. Organomet. Chem.*, 288, 63 (1985); *Japan Chemical Society ed. Organometallic complex* (4th ed. Experimental chemistry series No. 18), Maruzen (1991) p. 81 (in Japanese)), and in many cases a metallocene compound having the meso structure is produced as a byproduct in the nearly same amount as that having the racemic structure, whereby there is such a problem that the separation of the aimed racemic metallocene compound is tedious. Generally, since metallocene compounds having the meso structure decrease the efficiency as a stereoregular polymerization catalyst, they are removed by a combination of purifying operations such as column chromatographic, washing or recrystallizing methods (*J. Organomet. Chem.*, 232, 233 (1982); *J. Organomet. Chem.*, 369, 359 (1989); *Chem. Lett.*, 1853 (1989), *Organometallics*, 10, 1501 (1991); *J. Organomet. Chem.*, 415, 75 (1991); *Organometallics*, 13 954 (1994); *J. Organomet. Chem.*, 497, 43 (1995).

Thus, the conventional synthetic methods give a considerable amount of meso metallocene compounds as byproducts, therefore, the yields of racemic metallocene compounds are low, and due to the fact that the procedure in the purification step is tedious, the cost of the synthesis is high, and it is difficult to carry out in an industrial scale.

As a trial for solving such problems is reported the method that after the reaction only the metallocene compounds having the racemic structure are crystallized by appropriately selecting the reaction solvent used(JP, A, 6-122692; U.S. Pat. No. 5,391,790; U.S. Pat. No. 5,616, 747). However, in this method the metallocene compound having meso structure is still produced in a nearly half amount, therefore, it can hardly be said that this is an efficient synthetic method.

Further, although the methods by which the metallocene compounds having the meso structure are converted to the metallocene compounds having the racemic structure are studied (*J. Organomet. Chem.*, 342, 21 (1988); *Organometallics*, 11, 1869 (1992)), pure racemic metallocene compounds cannot be obtained, and furthermore, the decomposition of the metallocene compounds occurs.

On the other hand, the method to selectively synthesize the metallocene compounds having the racemic structure is also reported. In the methods using a ligand in which a bulky substituent is introduced to a cyclopentadienyl skeleton and a ligand having a binaphtyl skeleton in a bridging part, they give low yields and are impractical (*Organometallics*, 10, 2349 (1991); *Organometallics*, 10, 2998 (1991)). The method to carry out the reaction at the low reaction temperature of −78° C. is also proposed (JP, A, 1-197490; U.S. Pat. No. 5,103,030), but the yield expected is not obtained. Further, in the synthetic examples of metallocene compounds having the pseudo-racemic structure are used a ligand having the special structure in which 2-position of a indenyl group is bridged by a biaryl group, and the method is practically poor (*Organometallics*, 12, 2879 (1993); *Organometallics*, 12, 4391 (1993)). Also, a method employing $(CH_3)_2ZrCl_2$ has been studied, but the selectivity of the racemic structure amounts at most around 75% in this method. Moreover this might cause trouble in that the reaction tends to take place to predominantly form a meso-type depending on the structure of the ligand (*J. Organomet. Chem.*, 535, 29 (1997)).

On the contrary are reported the methods to obtain the metallocene compounds having the racemic structure in high yields by reacting $Zr(NMe_2)_4$ with a ligand (WO 95/32979; U.S. Pat. No. 5,495,035; *Organometallics*, 14, 5 (1995); *J. Am. Chem. Soc.*, 118, 8024 (1996)). However, these methods require such a long time as 3–24 hours at the reaction temperature of 80°–160° C., usually 100° C. In the reaction condition, in which heating is required for long time like this, the polymerization or the decomposition of a ligand , which is unstable for heat, occur and it makes the yield low. Additionally, due to the fact that dimethylamine, the starting material of $Zr(NMe_2)_4$, is a gas (b.p. 7° C.) at room temperature, a special reaction equipment corresponding to the gas reaction to prepare $Zr(NMe_2)_4$ is necessary. Further, on the treatment there are various kinds of difficulties such that $Zr(NMe_2)_4$ is very unstable in the presence of air.

SUMMARY OF THE INVENTION

Under these circumstances, the inventors made an intensive studies to develop a synthetic method of metallocene compounds having the racemic structure and found that new metallocene compounds having the racemic structure of the general formula (II) can be efficiently synthesized by using new transition metal compounds of the general formula (I), lowering the occurrence of tarry substances and metallocene compounds having the meso structure. The invention is based on this finding.

The invention provides the compounds described below.
1) New organotransition metal compounds of the general formula (I)

(wherein $M^1$ is a group IV transition metal atom, A is a nitrogen or phosphorus atom, $R^1$ is a aryl group, $R^2$ is a saturated hydrocarbon group having 1–10 carbon atoms, whereby each of $R^2$ can bind one another to constitute a ring containing A and $M^1$, X can be identical or different and is each independently of one another a halogen atom, and $M^1$ can be also coordinated with an ether or an amine at any coordination number, provided that when $R^2$ is a saturated hydrocarbon group having one carbon atom, and $M^1$ is a zirconium atom whereby each of $R^2$ binds one another to constitute a ring containing A and $M^1$, then $M^1$ is not coordinated with two molecules of 1,4-dioxanes.) are provided.
2) New metallocene compounds having the racemic structure of the general formula (II)

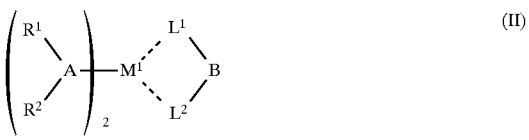

(wherein $M^1$ is a group IV transition metal atom, A is a nitrogen or phosphorus atoms, $R^1$ is an aryl group, $R^2$ is a saturated hydrocarbon group having 1–10 carbon atoms, whereby each of $R^2$ can bind one another to constitute a ring containing A and $M^1$, $L^1$ and $L^2$ can be each other identical or different and are a substituted cyclopentadienyl, indenyl, substituted indenyl or substituted fluorenyl groups, B is a hydrocarbon having 1–20 carbon atoms, silylene having 1–20 carbon atoms, oligosilylene or germylene groups, binding to $L^1$ and $L^2$, and $M^1$ can be also coordinated with an ether or an amine at any coordination number.) are provided.

Usually, as a starting material for the synthesis of metallocene compounds are used group IV transition metal compounds having four same leaving groups (Illustrative of an example are zirconium tetrachloride or tetrakisdimethylamidozirconium.). The inventors found out the compounds of the general formula (I), that is, group IV transition metal compounds containing two leaving groups and two groups in which an aryl group and a hydrocarbon group bind to hetero atoms. To be surprised, when a compound of the general formula (I) was reacted with a deprotonated ligand, the occurrence of tarry substances or a metallocene compound having the meso structure as byproducts was suppressed, and it was found out that a new metallocene compound of the general formula (II) could be efficiently synthesized (see the below scheme 2). The compounds of the general formula (II) are expected not only to have a catalytic action in themselves, but also are useful substances which can be converted to dihalogenometallocene compounds useful as an olefin polymerazation catalyst. Consequently, the new compounds of the general formula (I) and (II) are extremely important for those skilled in the art from the industrial view point.

Scheme 2

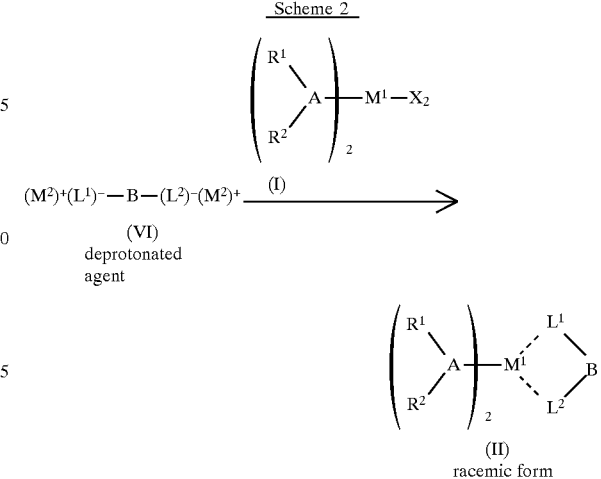

racemic form

In the following, the invention will be explained in detail.

As similar compounds to the compounds of the general formula (I) are known compounds, whereby $R^1$ and $R^2$ are both methyl, ethyl or phenyl group (*Z. Anorg. Allg. Chem.*, 621, 2021, (1995); JP, B, 42-22691), compounds, whereby $R^2$ is a hydrocarbon group containing deuterium (*Organometallics*, 13, 2907 (1994); *Organometallics*, 15, 3825 (1996)), and compounds, whereby R² is a saturated hydrocarbon group having one carbon atom, M¹ is a zirconium atom coordinated with two molecules of 1,4-dioxane and each of R² binds one another to constitute a ring containing A and M¹ (*Z. Chem.*, 14, 486 (1974)). The inventors succeeded in synthesizing new compounds of the general formula (I). Illustrative of the compounds of the general formula (I) are, for example, bis(N-methylanilido) titanium difluoride.bis tetrahydrofuran, bis(N-ethylanilido) titanium difluoride.bis tetrahydrofuran, bis(N-propylanilido) titanium difluoride.bis tetrahydrofuran, bis(N-butylanilido) titanium difluoride.bis tetrahydrofuran, bis((N-methyl) toluylamido)titanium difluoride-bis tetrahydrofuran, bis((N-ethyl)toluylamido)titanium difluoride.bis tetrahydrofuran, bis((N-propyl)toluylamido)titanium difluoride.bis tetrahydrofuran, bis((N-butyl)toluylamido)titanium difluoride.bis tetrahydrofuran, bis((N-methyl)dimethylphenylamido)titanium difluoride.bis tetrahydrofuran, bis((N-ethyl)dimethylphenylamido)titanium difluoride.bis tetrahydrofuran, bis((N-propyl)dimethylphenylamido)titanium difluoride.bis tetrahydrofuran, bis((N-butyl)dimethylphenylamido)titanium difluoride.bis tetrahydrofuran, N,N'-diphenylethylenediamidotitanium difluoride.bis tetrahydrofuran, bis(N-methylanilido)zirconium difluoride.bis tetrahydrofuran, bis(N-ethylanilido)zirconium difluoride.bis tetrahydrofuran, bis(N-propylanilido) zirconium difluoride.bis tetrahydrofuran, bis(N-butylanilido)zirconium difluoride.bis tetrahydrofuran, bis((N-methyl)toluylamido)zirconium difluoride.bis tetrahydrofuran, bis((N-ethyl)toluylamido)zirconium difluoride.bis tetrahydrofuran, bis((N-propyl)toluylamido) zirconium difluoride.bis tetrahydrofuran, bis((N-butyl) toluylamido)zirconium difluoride.bis tetrahydrofuran, bis( (N-methyl)dimethylphenylamido)zirconium difluoride.bis tetrahydrofuran, bis((N-ethyl)dimethylphenylamido) zirconium difluoride.bis tetrahydrofuran, bis (dimethylphenylpropylamido)zirconium difluoride.bis tetrahydrofuran, bis((N-butyl) dimethylphenylamido) zirconium difluoride.bis tetrahydrofuran, N,N'-diphenylethylenediamidozirconium difluoride.bis tetrahydrofuran, bis(N-methylanilido)hafnium difluoride.bis tetrahydrofuran, bis(N-ethylanilido)hafnium difluoride.bis tetrahydrofuran, bis(N-propylanilido) hafnium difluoride.bis tetrahydrofuran, bis(N-butylanilido)hafnium difluoride.bis tetrahydrofuran, bis((N-methyl) toluylamido)hafnium difluoride.bis tetrahydrofuran, bis((N-ethyl)toluylamido) hafnium difluoride.bis tetrahydrofuran, bis((N-propyl) toluylamido)hafnium difluoride.bis tetrahydrofuran, bis((N-butyl) toluylamido)hafnium difluoride.bis tetrahydrofuran, bis((N-methyl)dimethylphenylamido)hafnium difluoride.bis tetrahydrofuran, bis((N-ethyl)dimethylphenylamido) hafnium difluoride.bis tetrahydrofuran, bis((N-propyl) dimethylphenylamido)hafnium difluoride.bis tetrahydrofuran, bis((N-butyl)dimethylphenylamido) hafnium difluoride.bis tetrahydrofuran, N,N'-diphenylethylenediamidohafnium difluoride.bis tetrahydrofuran, bis(N-methylanilido)titanium dichloride.bis tetrahydrofuran, bis(N-ethylanilido)titanium dichloride.bis tetrahydrofuran, bis(N-propylanilido)titanium dichloride.bis tetrahydrofuran, bis(N-butylanilido)titanium dichloride.bis tetrahydrofuran, bis((N-methyl)toluylamido) titanium dichloride.bis tetrahydrofuran, bis((N-ethyl) toluylamido)titanium dichloride.bis tetrahydrofuran, bis((N-propyl)toluylamido)titanium dichloride.bis tetrahydrofuran, bis((N-butyl)toluylamido)titanium dichloride.bis tetrahydrofuran, bis((N-methyl)dimethylphenylamido) titanium dichloride.bis tetrahydrofuran, bis((N-ethyl) dimethylphenylamido)titanium dichloride.bis tetrahydrofuran, bis((N-propyl)dimethylphenylamido) titanium dichloride.bis tetrahydrofuran, bis((N-butyl) dimethylphenylamido)titanium dichloride.bis tetrahydrofuran, N,N'-diphenylethylenediamidotitanium dichloride.bis tetrahydrofuran, bis(N-methylanilido) zirconium dichloride.bis tetrahydrofuran, bis(N-ethylanilido)zirconium dichloride.bis tetrahydrofuran, bis (N-propylanilido)zirconium dichloride.bis tetrahydrofuran, bis(N-butylanilido)zirconium dichloride.bis tetrahydrofuran, bis((N-methyl) toluylamido)zirconium dichloride.bis tetrahydrofuran, bis((N-ethyl)toluylamido) zirconium dichloride.bis tetrahydrofuran, bis((N-propyl) toluylamido)zirconium dichloride.bis tetrahydrofuran, bis( (N-butyl) toluylamido)zirconium dichloride.bis tetrahydrofuran, bis((N-methyl)dimethylphenylamido) zirconium dichloride.bis tetrahydrofuran, bis((N-ethyl) dimethylphenylamido)zirconium dichloride.bis tetrahydrofuran, bis((N-propyl) dimethylphenylamido) zirconium dichloride.bis tetrahydrofuran, bis((N-butyl) dimethylphenylamido)zirconium dichloride.bis tetrahydrofuran, N,N'-diphenylethylenediamidozirconium dichloride.bis tetrahydrofuran, bis(N-methylanilido) hafnium dichloride.bis tetrahydrofuran, bis(N-ethylanilido) hafnium dichloride.bis tetrahydrofuran, bis(N-propylanilido)hafnium dichloride.bis tetrahydrofuran, bis (N-butylanilido)hafnium dichloride.bis tetrahydrofuran, bis ((N-methyl)toluylamido)hafnium dichloride.bis tetrahydrofuran, bis((N-ethyl) toluylamido)hafnium dichloride.bis tetrahydrofuran, bis((N-propyl)toluylamido) hafnium dichloride.bis tetrahydrofuran, bis((N-butyl) toluylamido)hafnium dichloride.bis tetrahydrofuran, bis((N-methyl) dimethylphenylamido)hafnium dichloride.bis tetrahydrofuran, bis((N-ethyl)dimethylphenylamido) hafnium dichloride.bis tetrahydrofuran, bis((N-propyl) dimethylphenylamido)hafnium dichloride.bis tetrahydrofuran, bis((N-butyl)dimethylphenylamido) hafnium dichloride.bis tetrahydrofuran, N,N'-diphenylethylenediamidohafnium dichloride.bis tetrahydrofuran, bis(N-methylanilido)titanium dibromide.bis tetrahydrofuran, bis(N-ethylanilido)titanium dibromide.bis tetrahydrofuran, bis(N-propylanilido) titanium dibromide.bis tetrahydrofuran, bis(N-butylanilido) titanium dibromide.bis tetrahydrofuran, bis((N-methyl) toluylamido)titanium dibromide.bis tetrahydrofuran, bis((N-ethyl)toluylamido)titanium dibromide.bis tetrahydrofuran, bis((N-propyl) toluylamido)titanium dibromide.bis tetrahydrofuran, bis((N-butyl)toluylamido)titanium dibromide.bis tetrahydrofuran, bis((N-methyl) dimethylphenylamido)titanium dibromide.bis tetrahydrofuran, bis((N-ethyl) dimethylphenylamido) titanium dibromide.bis tetrahydrofuran, bis((N-propyl) dimethylphenylamido)titanium dibromide.bis tetrahydrofuran, bis((N-butyl) dimethylphenylamido) titanium dichloride.bis tetrahydrofuran, N,N'-diphenylethylenediamidotitanium dibromide.bis tetrahydrofuran, bis(N-methylanilido)zirconium dibromide.bis tetrahydrofuran, bis(N-ethylanilido) zirconium dibromide.bis tetrahydrofuran, bis(N-propylanilido)zirconium dibromide.bis tetrahydrofuran, bis (N-butylanilido)zirconium dibromide.bis tetrahydrofuran, bis((N-methyl) toluylamido)zirconium dibromide.bis tetrahydrofuran, bis((N-ethyl)toluylamido)zirconium dibromide.bis tetrahydrofuran, bis((N-propyl)toluylamido) zirconium dibromide.bis tetrahydrofuran, bis((N-butyl) toluylamido)zirconium dibromide.bis tetrahydrofuran, bis( (N-methyl)dimethylphenylamido)zirconium dibromide.bis tetrahydrofuran, bis((N-ethyl)dimethylphenylamido) zirconium dibromide.bis tetrahydrofuran, bis((N-propyl) dimethylphenylamido)zirconium dibromide.bis tetrahydrofuran, bis((N-butyl)dimethylphenylamido) zirconium dibromide.bis tetrahydrofuran, N,N'-diphenylethylenediamidozirconiumdibromide.bis tetrahydrofuran, bis(N-methylanilido)hafnium dibromide.bis tetrahydrofuran, bis(N-ethylanilido)hafnium dibromide.bis tetrahydrofuran, bis(N-propylanilido)hafnium dibromide.bis tetrahydrofuran, bis(N-butylanilido)hafnium dibromide.bis tetrahydrofuran, bis((N-methyl)toluylamido) hafnium dibromide.bis tetrahydrofuran, bis((N-ethyl) toluylamido)hafnium dibromide.bis tetrahydrofuran, bis((N-propyl) toluylamido)hafnium dibromide.bis tetrahydrofuran, bis ((N-butyl) toluylamido) hafniumdibromide bis tetrahydrofuran, bis((N-methyl) dimethylphenylamido)hafnium dibromide.bis tetrahydrofuran, bis((N-ethyl)dimethylphenylamido) hafnium dibromide.bis tetrahydrofuran, bis((N-propyl) dimethylphenylamido)hafnium dibromide.bis tetrahydrofuran, bis((N-butyl)dimethylphenylamido) hafnium dibromide.bis tetrahydrofuran, N,N'-diphenylethylenediamidohafnium dibromide.bis tetrahydrofuran or compounds having the structure in which a nitrogen atom of each of the above compounds is replaced by a phosphorus atom or compounds substituted by diethyl ether instead of the tetrahydrofuran of the above compounds.

In order to synthesize the compounds of the general formula (I) can be applied the method that a tetrahalogenometal compound is converted to a tetrakisamidometal or tetrakisphosphinometal compounds, followed by the disproportionation with the tetrahalogenometal compound in solvent (JP, B, 42-22691; *Organometallics*, 13, 2901 (1994); *Z. Anorg. Allg. Chem.*, 621, 2021, (1995)), and the method of the below Scheme 3. The aimed compounds can be synthesized from the starting tetrahalogenometal compounds in one step by means of the method shown in Scheme 3

Formula 3

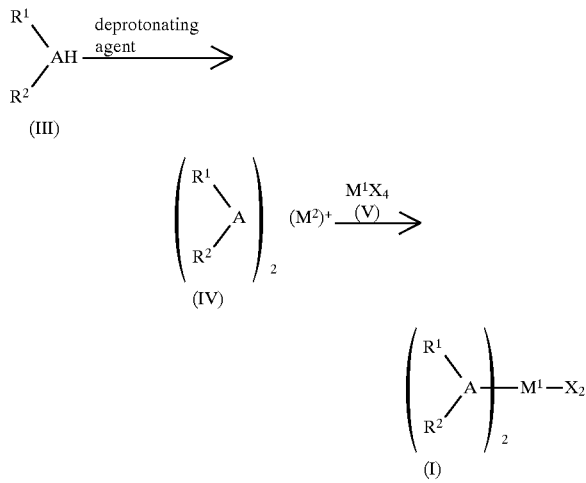

The reaction of Scheme 3 can be carried out in a good yield, first, by deprotonating a compound of the general formula (III)

(wherein A is a nitrogen or phosphorus atoms, $R^1$ is a aryl group, $R^2$ is a saturated hydrocarbon group having 1–10 carbon atoms.) to afford the compound of the general formula (IV)

(wherein A is a nitrogen or phosphorus atoms, $R^1$ is a aryl group, $R^2$ is a saturated hydrocarbon group having 1–10 carbon atoms, and $M^2$ is an alkaline or alkaline earth metals and can be also coordinated with an ether or an amine at any coordination number.), which is reacted with a compound of the general formula (V)

$$M^1X_4 \quad (V)$$

(wherein $M^1$ is a group IV transition metal atom, X can be identical or different and is each independently of one another a halogen atom, and $M^1$ can be also coordinated with an ether or an amine at any coordination number.).

The deprotonation reaction of a compound of the general formula (III) is carried out by cooling the compound of the general formula (III) in a solvent below its boiling point, adding a deprotonating agent, and then stirring at room temperature for 30 min. to overnight, and the compounds of the general formula (IV) are obtained. Illustrative of the deprotonating agent are alkaline metals or alkaline earth metals such as Li, Na, K, LiH, NaH, KH, MeLi, n-BuLi, sec-BuLi or tert-BuLi, or solution thereof dissolved in organic solvents such as n-hexane, cyclohexane or diethyl ether, or the like.

The compounds of the general formula (V) are coordinated preferably with ethers or amines at any coordination number. The compounds of the general formula (V) to which ethers or amines are bound are obtained, for an example, by adding gradually noncoordinated $M^1X_4$ to ethers or amines undercooling. $TiCl_4.2THF$, $ZrCl_4.2THF$ and $HfCl_4.2THF$ are commercially available, and they can be used.

Furthermore, a compound of the general formula (V) of 0.4–0.6 equivalent mole, preferably 0.5 equivalent mole, is suspended or dissolved in solvent, added with a solution of a compound of the general formula (IV), and stirred for 30 min. to overnight. The reaction can be carried out at room temperature. Illustrative of the solvent used in the reaction are THF, diethyl ether, diisopropyl ether, n-pentane, n-hexane or toluene, or the like. After removing a salt bye-produced in the reaction solution, a new compound of the general formula (I) can be obtained by recrystallization.

Further, the compounds of the general formula (I) have a possibility to show the efficiency as an olefin polymerization catalyst under the coexistence of a cocatalyst such as aluminoxane or the like.

Furthermore, a process of synthesizing efficiently the metallocene compounds of the general formula (II) having the new racemic structure using the compounds of the general formula (I) will be explained.

The synthesis of the compounds of the general formula (II) is carried out by reacting the compounds of the general formula (I) with the compounds of the general formula (VI)

$$(M^2)^+(L^1)^--B-(L^2)^-(M^2)^+ \quad (VI)$$

(wherein $L^1$ and $L^2$ can be each other identical or different and are a substituted cyclopentadienyl, indenyl, substituted indenyl or substituted fluorenyl groups, B isa hydrocarbon having 1–20 carbon atoms, silylene having 1–20 carbon atoms, oligosilylene or germylene groups, binding to $L^1$ and $L^2$, and $M^2$ is an alkaline or alkaline earth metals and can be also coordinated with an ether or an amine at any coordination number.). The compounds of the general formula (VI) are known compounds which have been synthesized as starting materials for various metallocene compounds. Illustrative of $L^1$ and $L^2$ constituting the compounds of the general formula (VI) are, for example, 3-methylcyclopentadienyl, 2,4-dimethylcyclopentadienyl, 3-tert-butylcyclopentadienyl, 2,3,4,5-tetramethylcyclopentadienyl, indenyl, 2-methylindenyl, 2-methyl-4,5-benzoindenyl, 2-methyl-4-phenylindenyl, 2-methyl-4-naphthylindenyl or 2-tert-butylfluorenyl groups, or the like. Additionally, illustrative of B constituting the compounds of the general formula (VI) are ,for example, a methylene, ethylene, isopropylidene, diphenylmethylene, dimethylsilylene or diphenylsilylene groups, or the like.

The reaction of a compound of the general formula (I) and a compound of the general formula (VI) is carried out by suspending or dissolving the compound of the general formula (I) in solvent, adding then a solution of the compound of the general formula (VI) and stirring for 30 min. to overnight. The reaction does not especially require heating and usually, ends under stirring at room temperature for 30 min. to 3 hours. Illustrative of the solvent used in the reaction are THF, diethyl ether, diisopropyl ether, n-pentane or toluene, or the like, preferably THF, diethyl ether or diisopropyl ether. In the reaction is suppressed the occurrence of tarry substances and a metallocene compound having the meso structure, and the compound of the general formula (II) having the racemic structure is efficiently produced. The metallocene compound of the general formula (II) having the racemic structure can be isolated by removing a salt produced in the reaction solution.

Further, the compounds of the general formula (II) has a possibility to show the efficiency as an olefin polymerization catalyst under the coexistence of a cocatalyst such as aluminoxane or the like.

The compounds of the general formula (II) can easily be converted by the action of a halogenating agent on the halogenated metallocene compounds of the general formula (VII)

(VII)

(wherein $M^1$ is a group IV transition metal atom, $L^1$ and $L^2$ can be each other identical or different and are a substituted cyclopentadienyl, indenyl, substituted indenyl or substituted fluorenyl groups, B is a hydrocarbon having 1–20 carbon atoms, silylene having 1–20 carbon atoms, oligosilylene or germylene groups, binding to $L^1$ and $L^2$, Y can be identical or different and is each independently of one another a halogen atom, and $M^1$ can be also coordinated with an ether or an amine at any coordination number.).

Formula 4

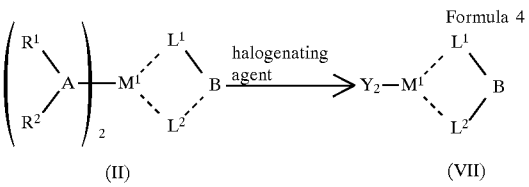

Illustrative of the compounds of the general formula (VII) are dimethylsilylenebis(3-methylcyclopentadienyl)titanium dichloride, ethylenebis(1-indenyl)titanium dichloride, diphenylsilylenebis (2-tert-butylfluorenyl) titanium dichloride, dimethylsilylenebis(3-methylcyclopentadienyl) zirconium dichloride, ethylenebis(1-indenyl)zirconium dichloride, diphenylsilylenebis(2-tert-butylfluorenyl) zirconium dichloride, dimethylsilylenebis(3-methylcyclopentadienyl) hafnium dichloride, ethylenebis(1-indenyl) hafnium dichloride, diphenylsilylenebis(2-tert-butylfluorenyl) hafnium dichloride, etc.

The halogenation is carried out by dissolving a metallocene compound of the general formula (II) in solvent, adding a halogenating agent at −78° C. to room temperature and stirring. As a halogenating agent can be used $Me_2NH.HCl$, HCl gas, conc. HCl or $Me_3SiCl$, or the like. Solvents such as THF, diethyl ether, toluene, chloroform, methylene chloride, trichloromethane, carbon tetrachloride, chlorobenzene or dichlorobenzene, or the like can be used.

In the following, the invention will be explained in more concrete way by examples, but it is to be understood that the invention is not limited thereby in any way. Further, all reactions in the examples were performed under an inert gas atmosphere of an argon or nitrogen gases or the like. Additionally, solvents used in the reactions were dried and degassed.

EXAMPLE 1

Synthesis of bis(N-methylanilido)zirconium dichloride.bistetrahydrofuran

N-Methylaniline (40.0 g) and THF (233 ml) were placed in a 1 liter Schlenk tube and cooled to 0° C. Subsequently, the mixture was dropped with a n-BuLi/n-hexane solution (1.68N, 233 ml) at the same temperature in 15 min, warmed to room temperature and stirred for 3.5 hours. Another 1 liter Schlenk tube prepared separately was charged with THF (160 ml) and $ZrCl_4$. 2THF (70.5 g), whereby the mixture was then dropped with the anion of N-methylaniline under stirring in 1 hour and stirred at room temperature for 3 hours. After the reaction, the solvent was distilled under reduced pressure to give the viscous liquid, which was extracted with methylene chloride (500 ml) to remove the insoluble LiCl. The solution was concentrated under reduced pressure to remove the solvent, followed by collecting precipitated crystals to give bis(N-methylanilido)zirconium dichloride-bistetrahydrofuran (77.0 g, 79% yield, yellow crystals). The analytical data are as follows, confirming the title compound.

$^1$H-NMR (90 MHz, $CDCl_3$/TMS) δ (ppm) 1.7–1.9 (m, THF, 8H), 3.36 (s, NMe, 6H), 4.0–4.2 (m, THF, 8H), 6.6–7.3 (m, phenyl, 10H).

Elemental analysis: Found. C, 49.90%; H, 6.088%; N, 5.326%. Calcd. C, 50.95%; H, 6.219%; N, 5.401%.

EXAMPLE 2

Synthesis of bis(N-methylanilido)zirconium dichloride.bisdiethyl ether

In the procedure described in Example 1, diethyl ether was used instead of THF as solvent, and $ZrCl_4.2Et_2O$ was used instead of $ZrCl_4 \cdot 2THF$. Except these, the reaction was carried out in the same way as that of Example 1 to give bis(N-methylanilido) zirconium dichloride.bisdiethyl ether (78% yield, a red viscous product). The analytical data are as follows, confirming the title compound.

$^1$H-NMR (90 MHz, $CDCl_3$/TMS) δ (ppm) 1.16 (t, J=7.03 Hz, $Et_2O$, 12H), 3.39 (s, NMe, 6H), 3.53 (q, J=7.03 Hz, $Et_2O$, 8H), 6.7–7.3 (m, phenyl, 10H).

EXAMPLE 3

Synthesis of bis(N-ethylanilido)zirconium dichloride.bistetrahydrofuran

Except that N-ethylaniline was used instead of N-methylaniline as the starting material in the procedure described in Example 1, the reaction was carried out in the same way as that of Example 1 to give bis(N-ethylanilido) zirconium dichloride-bistetrahydrofuran (72% yield, yellow crystals). The analytical data are as follows, confirming the title compound.

$^1$H-NMR (90 MHz, $CDCl_3$/TMS) δ (ppm) 1.05 (t, J=7.03 Hz, $CH_3$, 3H), 1.25 (t, J=7.03 Hz, $CH_3$, 3H), 1.81 (m, THF, 8H), 3.15 (q, J=7.03 Hz, $CH_2$, 2H), 3.19 (q, J=7.03 Hz, $CH_2$, 2H), 3.93 (m, THF, 8H), 6.6–7.3 (m, phenyl, 10H).

Elemental analysis: Found. C, 51.23%; H, 6.462%; N, 5.250%. Calcd. C, 52.73%; H, 6.637%; N, 5.124%.

EXAMPLE 4

Synthesis of bis(N-methylanilido)hafnium dichloride.bistetrahydrofuran

Except that $HfCl_4 \cdot 2THF$ was used instead of $ZrCl_4 \cdot 2THF$ as the starting material in the procedure described in Example 1, the reaction is carried out in the same way as that of Example 1 to give bis (N-methylanilido) hafnium dichloride.bistetrahydrofuran (74%, white crystals). The analytical data are as follows, confirming the title compound.

$^1$H-NMR (90 MHz, $CDCl_3$/TMS) δ (ppm) 1.75–1.90 (m, THF, 8H), 3.35 (s, NMe, 6H), 4.02–4.16 (m, THF, 8H), 6.6–7.4 (m, phenyl, 10H).

EXAMPLE 5

Synthesis of N,N'-diphenylethylenediamidotitanium dichloride-bistetrahydrofuran 1,2-Dianilinoethane was used as the starting material instead of N-methylaniline, and the n-BuLi/n-hexane solution of 2 equivalent mole against 1,2-dianilinoethane and $TiCl_4 \cdot 2THF$ of equivalent mole against 1,2-dianilinoethane instead of $ZrCl_4 \cdot 2THF$ were used in the procedure described in Example 1. Except these, the reaction was carried out in the same way as that of Example 1 to give N,N'-diphenylethylenediamidotitanium dichloride-bistetrahydrofuran (54% yield, dark red-brown powder) The analytical data are as follows, confirming the title compound.

1H-NMR (90 MHz, $CDCl_3$/TMS) δ (ppm) 1.5–2.2 (m, THF, 8H), 3.2–4.4 (m, $CH_2CH_2$, THF, 12H), 6.6–7.6 (m, phenyl, 10H).

EXAMPLE 6

Synthesis of N,N'-diphenylethylenediamidozirconium dichloride-bistetrahydrofuran Except that $ZrCl_4 \cdot 2THF$ was used instead of $TiCl_4 \cdot 2THF$ as the starting material in the procedure described in Example 5, the reaction is carried out in the same way as that of Example 5 to give N,N'-diphenylethylenediamidozirconium dichloride-bistetrahydrofuran (102%, yellow-ashy powder). The analytical data are as follows, confirming the title compound.

$^1$H-NMR (90 MHz, $CDCl_3$/TMS) δ (ppm) 1.6–2.0 (m, THF, 8H), 3.4–4.0 (m, $CH_2CH_2$, THF, 12H), 6.6–7.6 (m, phenyl, 1H).

EXAMPLE 7

Synthesis of ethylenebis(1-indenyl) zirconium bis (N-methylanilide)

1,2-Bis(3-indenyl)ethane (3.01 g) and THF (45.8 ml) were placed in a 100 ml Schlenk tube and cooled to 0° C. Subsequently, the mixture was dropped with a n-BuLi/n-hexane solution (1.57N, 15.2 ml) in 5 min. and stirred at room temperature for 1 hour. Another 200 ml Schlenk tube prepared separately was charged with bis(N-methylanilide) zirconium dichloride-bistetrahydrofuran (6.35 g) and THF (45.8 ml), whereby the mixture was then dropped with the anion of 1,2-bis(3-indenyl)ethane under stirring in 5 min. and stirred at room temperature for 1 hour. After the reaction, the solvent was distilled under reduced pressure to give the red-brown powder, which was extracted with methylene chloride (100 ml) to remove LiCl. The solution was evaporated under reduced pressure to give ethylenebis(1-indenyl)zirconium bis(N-methylanilide) of the racemic ratio not less than 95% (6.39 g, 98% yield) as red-brown powder. The analytical data are as follows, confirming the title compound.

$^1$H-NMR (90 MHz, $CDCl_3$/TMS) δ (ppm) 2.65 (s, NMe, 6H), 3.55–3.91 (m, Et, 4H), 5.95 (dd, J=3.30 Hz, J=0.88 Hz, $C_5$ring, 2H), 6.24 (d, J=3.30 Hz, $C_5$ring, 2H), 6.45–7.39 (m, $C_6$ring, 16H), 7.79 (ddd, J=0.88 Hz, J=8.35 Hz, J=0.88 Hz, $C_6$ring, 2H).

EXAMPLE 8

Synthesis of dimethylsilylenebis(2,4-dimethylcyclopentadienyl) zirconium bis(N-methylanilide)

Except that dimethylsilylenebis(2,4-dimethylcyclopentadiene) was used instead of 1,2-bis(3-indenyl) ethane as the starting material, the procedure is carried out in the same way as that of Example 7 to give dimethylsilylenebis(2,4-dimethylcyclopentadienyl) zirconium bis(N-methylanilide) (97%, red-brown powder).

EXAMPLE 9

Synthesis of ethylenebis(1-indenyl) zirconium bis (N-methylanilide)

Diethyl ether was used instead of THF as solvent, and the compound synthesized by the method described in Example 2 was used as the starting material. Except these, the procedure was carried out in the same way as that of Example 7 to give ethylenebis(1-indenyl)zirconium bis(N-methylanilide) of the racemic ratio not less than 95% (red-brown powder). The analytical data are as follows, confirming the title compound.

$^1$H-NMR (90 MHz, $CDCl_3$/TMS) δ (ppm) 2.65 (s, NMe, 6H), 3.55–3.91 (m, Et, 4H), 5.95 (dd, J=3.30 Hz, J=0.88 Hz, $C_5$ring, 2H), 6.24 (d, J=3.30 Hz, $C_5$ring, 2H), 6.45–7.39 (m, $C_6$ring, 16H), 7.79 (ddd, J=0.88 Hz, J=8.35 Hz, J=0.88 Hz, $C_6$ring, 2H).

EXAMPLE 10

Synthesis of ethylenebis(1-indenyl)zirconium bis(N-ethylanilide)

Except that the compound synthesized by the method described in Example 3 was used as the starting material, the procedure was carried out in the same way as that of Example 7 to give ethylenebis(1-indenyl)zirconium bis(N-ethylanilide) of the racemic ratio not less than 95% (118% yield) as red-brown powder The analytical data are as follows, confirming the title compound.

$^1$H-NMR (90 MHz, CDCl$_3$/TMS) δ (ppm) 0.71 (t, J=6.81 Hz, CH$_3$, 6H), 3.22 (q, J=6.81 Hz, CH$_2$, 4H), 3.73 (m, Et, 4H), 5.89 (dd, J=3.29 Hz, J=0.87 Hz, C$_5$ring, 2H), 5.96 (d, J=3.29 Hz, C$_5$ring, 2H), 6.55 (dd, J=8.57 Hz, J=1.54 Hz, C$_6$ring, 2H), 6.74–7.26 (m, C$_6$ring, 14H), 7.84 (ddd, J=0.88 Hz, J=8.57 Hz, J=0.88 Hz, C$_6$ring, 2H).

EXAMPLE 11

Synthesis of dimethylsilylenebis(1-indenyl)zirconium bis(N-methylanilide)

Except that dimethylsilylenebis(1-indene) was used instead of 1,2-bis(3-indenyl)ethane as the starting material, the procedure is carried out in the same way as that of Example 7 to give dimethylsilylenebis(1-indenyl)zirconium bis(N-methylanilide) of the racemic ratio not less than 95% (106% yield) as red-brown powder. The analytical data are as follows, confirming the title compound.

$^1$H-NMR (90 MHz, CDCl$_3$/TMS) δ (ppm) 1.16 (s, Si—Me, 6H), 2.53 (s, NMe, 6H), 6.34–7.85 (m, C$_6$ring, 22H).

EXAMPLE 12

Synthesis of ethylenebis(1-indenyl)zirconium bis (N,N'-diphenylethylenediamide)

Except that the compound synthesized by the method described in Example 6 was used as the starting material, the procedure was carried out in the same way as that of Example 7 to give ethylenebis(1-indenyl)zirconium bis (N,N'-diphenylethylenediamide) of the racemic ratio not less than 95% (111% yield) as brown powder. The analytical data are as follows, confirming the title compound.

$^1$H-NMR (90 MHz, CDCl$_3$/TMS) δ (ppm) 3.23–3.73 (m, Et, 8H), 6.08 (dd, J=1.32 Hz, J=1.10 Hz, C$_5$ring, 2H), 6.16 (d, J=1.32 Hz, C$_5$ring, 2H), 6.52–7.53 (m, C$_6$ring, 18H).

EXAMPLE 13

Synthesis of ethylenebis(1-indenyl)hafnium bis(N-methylanilide)

Except that the compound synthesized by the method described in Example 4 was used as the starting material, the procedure was carried out in the same way as that of Example 7 to give ethylenebis(1-indenyl)hafnium bis(N-methylanilide) of the racemic ratio not less than 95% (101% yield) as pale orange powder. The analytical data are as follows, confirming the title compound.

$^1$H-NMR (90 MHz, CDCl$_3$/TMS) δ (ppm) 2.70 (s, NMe, 6H), 3.78 (s, Et, 4H), 5.86 (dd, J=3.07 Hz, J=0.88 Hz, C$_5$ring, 2H), 6.11 (d, J=3.07 Hz, C$_5$ring, 2H), 6.32 (dd, J=8.57 Hz, J=1.31 Hz, C$_6$ring, 2H), 6.46–7.45 (m, C$_6$ring, 14H), 7.86 (ddd, J=0.88 Hz, J=8.57 Hz, J=1.10 Hz, C$_6$ring, 2H).

REFERENTIAL EXAMPLE 1

Halogenation of rac-dimethylsilylenebis(1-indenyl)zirconium bis(N-methylanilide)

rac-Dimethylsilylenebis(1-indenyl)zirconium bis (N-methylanilide) (0.976 g) and methylene chloride (10 ml) were placed in a 50 ml Schlenk tube and cooled to −78° C. Subsequently, the mixture was bubbled slowly with HCl gas, whereby the color of the solution turned from red to yellow, and then, the introduction of HCl gas was stopped. The mixture was concentrated under reduced pressure and recrystallized to give rac-dimethylsilylenebis(1-indenyl)zirconium dichloride (0.381 g, 54% yield based on bis(N-methylanilido)zirconium dichloride.bistetrahydrofuran). The analytical data are as follows, confirming the title compound.

$^1$H-NMR (90 MHz, CDCl$_3$/TMS) δ (ppm) 1.14 (s, Si—Me, 6H), 6.11 (d, J=3.30 Hz, C$_5$ring, 2H), 6.83 (dd, J=3.30 Hz, J=0.88 Hz, C$_5$ring, 2H), 7.0–7.7 (m, C$_6$ring, 8H).

REFERENTIAL EXAMPLE 2

Halogenation of rac-ethylenebis(1-indenyl)zirconium bis(N-methylanilide)

rac-Ethylenebis(1-indenyl)zirconium bis(N-methylanilide) (6.39 g) and methylene chloride (250 ml) were placed in a 500 ml Schlenk tube and cooled to −78° C. Subsequently, the mixture was bubbled slowly with HCl gas, whereby the color of the solution turned from red to yellow, and then, the introduction of HCl gas was stopped. The mixture was concentrated under reduced pressure and recrystallized to give rac-ethylenebis(1-indenyl)zirconium dichloride (3.0 g, 62% yield based on 1, 2-bis (3-indenyl) ethane). The analytical data are as follows, confirming the title compound.

$^1$H-NMR (90 MHz, CDCl$_3$/TMS) δ (ppm) 3.75 (s, Et, 4H), 6.20 (d, J=3.30 Hz, C$_5$ring, 2H), 6.58 (dd, J=3.30 Hz, J=0.88 Hz, C$_5$ring, 2H), 7.1–7.7 (m, C$_6$ring, 8H).

REFERENTIAL EXAMPLE 3

Halogenation of rac-ethylenebis(1-indenyl)hafnium bis(N-methylanilide)

rac-Ethylenebis(1-indenyl)hafnium bis(N-methylanilide) (4.62 g) and methylene chloride (20 ml) were placed in a 50 ml Schlenk tube and cooled to −78° C. Subsequently, the mixture was bubbled slowly with HCl gas, whereby the color of the solution turned from orange to yellow, and then, the introduction of HCl gas was stopped. The mixture was concentrated under reduced pressure and recrystallized to give rac-ethylenebis(1-indenyl) hafnium dichloride (1.84 g, 51% yield based on bis(N-methylanilido)hafnium dichloride-bistetrahydrofuran). The analytical data are as follows, confirming the title compound.

$^1$H-NMR (90 MHz, CDCl$_3$/TMS) δ (ppm) 3.80 (s, Et, 4H), 6.10 (d, J=3.30 Hz, C$_5$ring, 2H), 6.47 (dd, J=3.30 Hz, J=0.88 Hz, C$_5$ring, 2H), 7.1–7.7 (m, C$_6$ring, 8H).

What is claimed is:

1. An organotransition metal compound of the general formula (I)

wherein $M^1$ is a group IV transition metal atom, A is a nitrogen or phosphorus atom, $R^1$ is a aryl group, $R^2$ is a saturated hydrocarbon group having 1–10 carbon atoms whereby each of $R^2$ can bind one another to constitute a ring containing A and $M^1$, X can be identical or different and is each a halogen atom and $M^1$ can be also coordinated with an ether or an amine at any coordination number, provided that when $R^2$ is a saturated hydrocarbon group having one carbon atom, and $M^1$ is a zirconium atom whereby each of $R^2$ binds one another to constitute a ring containing A and $M^1$, then $M^1$ is not coordinated with two molecules of 1,4-dioxane, and when $R^1$ is 3,5-$C_6H_3Me_2$, A is a nitrogen atom, $M^1$ is a titanium atom and X is a iodine atom, then $R^2$ is not a tert-butyl.

2. The compound according to claim 1 wherein A in the above general formula (I) is a nitrogen atom.

3. The compound according to claim 1 wherein $R^2$ in the above general formula (I) is a saturated hydrocarbon group having 1–3 carbon atoms, whereby each can bind to constitute a ring containing A and $M^1$.

4. A metallocene compound having the racemic structure of the general formula (II)

wherein $M^1$ is a group IV transition metal atom, A is a nitrogen or phosphorous atom, $R^1$ is a aryl group, $R^2$ is a saturated hydrocarbon group having 1–10 carbon atoms, whereby each of $R^2$ can bind one another to constitute a ring containing A and $M^1$, $L^1$ and $L^2$ can be each identical or different and are a substituted cyclopentadienyl, indenyl, substituted indenyl or substituted fluorenyl groups, B is a hydrocarbon having 1–20 carbon atoms, silylene having 1–20 carbon atoms, oligosilylene or germylene groups, binding to $L^1$ and $L^2$, and $M^1$ can be also coordinated with an ether or an amine at any coordination number.

5. The compound according to claim 4, wherein A in the above general formula (II) is a nitrogen atom.

6. A method for synthesizing a metallocene compound having the racemic structure of the general formula (II)

wherein $M^1$ is a group IV transition metal atom, A is a nitrogen or phosphorous atom, $R^1$ is a aryl group, $R^2$ is a saturated hydrocarbon group having 1–10 carbon atoms, whereby each of $R^2$ can bind one another to constitute a ring containing A and $M^1$, $L^1$ and $L^2$ can be each identical or different and are a substituted cyclopentadienyl, indenyl, substituted indenyl or substituted fluorenyl groups, B is a hydrocarbon having 1–20 carbon atoms, silylene having 1–20 carbon atoms, oligosilylene or germylene groups, binding to $L^1$ and $L^2$, and $M^1$ can be also coordinated with an ether or an amine at any coordination number, by reacting (a) an organotransition metal compound of the general formula (I)

wherein $M^1$ is a group IV transition metal atom. A is a nitrogen or phosphorus atom, $R^1$ is a aryl group, $R^2$ is a saturated hydrocarbon group having 1–10 carbon atoms, whereby each of $R^2$ can bind one another to constitute a ring containing A and $M^1$, X can be identical or different and is each a halogen atom, and $M^1$ can be also coordinated with an ether or an amine at any coordination number, provided that when $R^2$ is a saturated hydrocarbon group having one carbon atom, and $M^1$ is a zirconium atom whereby each of $R^2$ binds one another to constitute a ring containing A and $M^1$, then $M^1$ is not coordinated with two molecules of 1,4 -dioxane; with (b) a compound of general formula (VI)

$(M^2)^+(L^1)^- \text{-B-}(L^2)^-(M^2)^+$      (VI)

wherein $L^1$ and $L^2$ can be each identical or different and are substituted cyclopentadienyl, indenyl, substituted indenyl or substituted fluorenyl groups, B is a hydrocarbon having 1–20 carbon atoms, silylene having 1–20 carbon atoms, oligosilylene or germylene groups, binding to $L^1$ and $L^2$, and $M^2$ is an alkaline or alkaline earth metals and can be also coordinated with an ether or an amine at any coordination number.

7. A method for synthesizing a metallocene compound according to claim 6 wherein A in the above general formula (I) is a nitrogen atom.

8. A method for synthesizing a metallocene compound according to claim 6 wherein $R^2$ in the above general formula (I) is a saturated hydrocarbon group having 1–3 carbon atoms, whereby each can bind to constitute a ring containing A and $M^1$.

* * * * *